United States Patent [19]
Yoshida et al.

[11] Patent Number: 5,137,807
[45] Date of Patent: Aug. 11, 1992

[54] METHOD FOR DETERMINING BETA-SUBUNIT OF HUMAN PROLYL 4-HYDROXYLASE BY IMMUNOASSAY TO DETECT HEPATIC DISEASE

[75] Inventors: Shinichi Yoshida, Toyama; Eiji Ishikawa, Miyazaki; Akira Oshima, Wakayama; Yasuo Bai, Osaka; Yasuteru Muragaki, Wakayama; Kazushi Iwata, Toyama; Kenichi Obata, Toyama; Yasuo Nagai, Toyama, all of Japan

[73] Assignee: Fuji Yakuhin Kogyo Kabushiki Kaisha, Toyama, Japan

[21] Appl. No.: 380,751

[22] Filed: Jul. 17, 1989

Related U.S. Application Data
[63] Continuation of Ser. No. 836,739, Mar. 6, 1986, abandoned.

[30] Foreign Application Priority Data
Mar. 6, 1985 [JP] Japan .................................. 60-42686

[51] Int. Cl.$^5$ ................................ C12Q 1/26
[52] U.S. Cl. .......................... 435/7.1; 435/25; 436/86; 436/518; 436/811; 436/820
[58] Field of Search .............................. 435/7, 25, 7.1; 436/518, 541, 804, 811, 820

[56] References Cited
PUBLICATIONS
Mansurova et al., *Lab Delo*, vol. 7, pp. 392–395 (1984).
*Methods in Enzymology*, vol. XVII B, Tabor et al. (ed.), Academic Press, N.Y., pp. 306–316 (1971).
Mansurova et al., *Chemical Abstracts*, vol. 101(15): 125495a (1984).

*Primary Examiner*—Sam Rosen
*Attorney, Agent, or Firm*—Birch, Stewart, Kolasch & Birch

[57] ABSTRACT

The present invention is directed to a method for detecting hepatic diseases which are associated with fibrosis by determining the level of human prolyl hydroxylase in a serum sample which comprises:

(a) contacting a serum sample of a patient suspected of having said hepatic disease associated with fibrosis with a monoclonal antibody specific to the β-subunit of human prolyl hydroxylase to form an antigen antibody complex bound on a solid support;

(b) contacting said antigen antibody complex bound on said solid support with an enzyme-labeled monoclonal or enzyme-labeled polyclonal antibody specific to human prolyl hydroxylase to form an antibody antigen enzyme-labeled antibody complex; and (c) measuring the amount of enzyme activity of said bound antibody antigen enzyme-labeled antibody complex to determine the level of human prolyl hydroxylase present in said serum sample.

2 Claims, 6 Drawing Sheets

METHOD FOR DETERMINING BETA-SUBUNIT OF HUMAN PROLYL 4-HYDROXYLASE BY IMMUNOASSAY TO DETECT HEPATIC DISEASE

BACKGROUND OF THE INVENTION

1. Field of the Invention:

This invention relates to a method for determining human prolyl 4-hydroxylase, which is useful for the straightforward diagnosis of hepatic diseases.

More particularly, this invention relates to a method for determining human prolyl 4-hydroxylase by enzyme immunoassay according to the sandwich technique using a specific monoclonal antibody and/or a polyclonal antibody.

2. Description of the Prior Art:

Among methods known hitherto for determining human prolyl 4-hydroxylase (referred to hereinafter simply as hPH) in human blood is included a method wherein 4-L-proline in protocollagen labeled with $^3H$ is used as a substrate and the resultant H labeled water is captured by vacuum distillation and measured for its radioactivity (Hutton et al., Anal. Biochem., 16, 384-394, 1966). Other known methods involve the use of $^{14}C$-proline labeled protocollagen as a substrate followed by the measurement of radioactivity from the resultant 4-hydroxylated $^{14}C$-proline (Juva et al., Anal. Biochem. 15, 77-83, 1966); or the use of (pro-pro-gyl)$_5$ or (pro-pro-gyl)$_{10}$ as a substrate followed by the capture and measurement of $^{14}CO_2$ released from 2-oxo(1-$^{14}C$)-glutaric acid (Berg et al., J. Biol. Chem., 248, 1175-1182, 1973). Any of these methods, however, has the disadvantages of requiring complicated, tremendous operations and time-consuming measurements. Furthermore, a simple measurement of hPH activity in blood does not reflect the true hPH level, because most of the hPH is present in blood in an enzymologically inactivated state.

Under the circumstances described above, it was quite impossible to measure the quantity of hPH precisely in a simple manner by way of an enzymatic activity-measuring method. Consequently, there is a great demand for developing a new method for effectively and precisely determining hPH in a simple manner in place of the conventional methods accompanied with various disadvantages, especially in the field of diagnosis of hepatic diseases.

BRIEF SUMMARY OF THE INVENTION

Accordingly, it is an object of the present invention to provide a method for the enzyme immunoassay of hPH applicable to the diagnosis of hepatic diseases.

It is another object of the present invention to provide a method for determining hPH by enzyme immunoassay according to the sandwich technique using a specific monoclonal and/or a polyclonal antibody to hPH without accompanying drawbacks as seen in the conventional methods.

It is still another object of the present invention to provide a method for determining hPH by enzyme immunoassay according to the sandwich technique with a smaller amount of samples in a simple operation.

Other objects, features and advantages of the present invention will become apparent as the description proceeds.

DETAILED DESCRIPTION OF THE INVENTION

Figure 1:
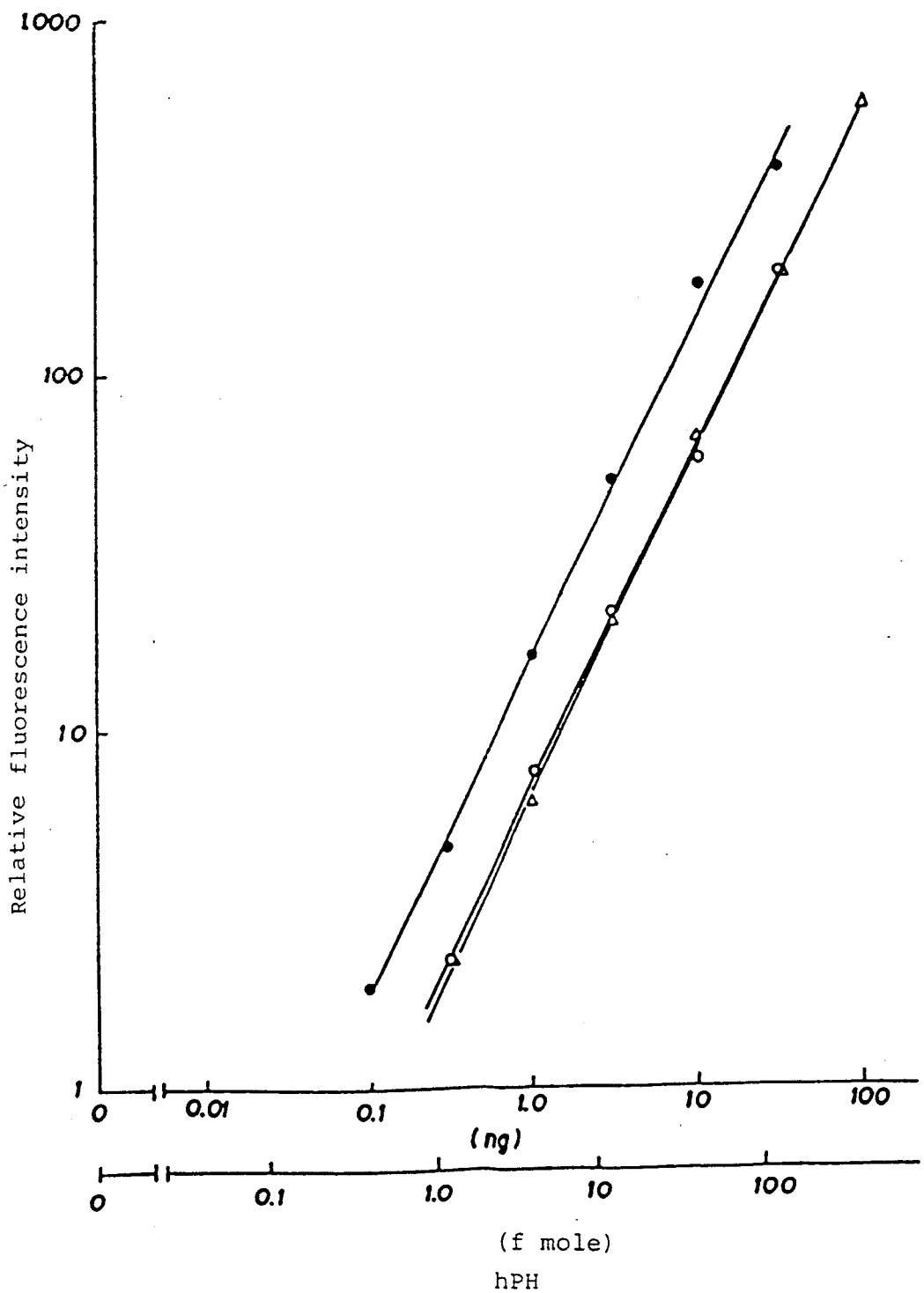
FIGS. 1 and 2 show hPH standard curves.

As a result of extensive research made by the present inventors for developing a simple method for determining hPH in a more straightforward and specific manner, it has now been found that a precise and rapid determination of hPH can be carried out with a smaller amount of samples by a method utilizing an enzyme immunoassay (EIA) according to the sandwich technique using a monoclonal and/or polyclonal antibody to hPH.

In accordance with the present invention, there is provided a method for determining hPH by enzyme immunoassay according to the sandwich technique using a monoclonal antibody and/or a polyclonal antibody each to hPH, characterized in that either of the monoclonal antibody or the polyclonal antibody is used as an antibody to be coated onto a solid phase and either of the monoclonal antibody or the polyclonal antibody is used as an antibody to be labeled with an enzyme.

The specific monoclonal antibody employed in the method of this invention is an anti-human prolyl 4-hydroxylase antibody of the IgG, IgA and IgM classes, which is obtained by immunizing an animal such as a mouse with hPH to form a hybridoma from anti-human prolyl 4-hydroxylase antibody-producing cells of the animal and myeloma cells, cloning the hybridoma and thereafter selecting and cultivating clones capable of producing anti-human prolyl 4-hydroxylase antibody having reactivity with the hPH. This monoclonal antibody has an immunocross-reactivity with any one of the antigenic determinants existing in hPH. This monoclonal antibody can be purified, if necessary, by fractionation with a sulfate such as ammonium sulfate followed by column chromatography with DEAE-Sephacel (Pharmacia Fine Chemicals) equilibrated with a buffer of a particular pH value.

The polyclonal antibody employed in the method of this invention is obtained by immuninzing an animal such as a rabbit with hPH, taking blood from the immunized animal and purifying the resultant anti-serum.

Employed as the antibody to be labeled with an enzyme in the method of this invention is an IgG fraction obtainable by the fractionation of a material containing antibodies with ammonium sulfate or sodium sulfate and the subsequent purification on a DEAE-cellulose column. In the case of the polyclonal antibody, it is preferred to carry out further purification on a Sepharose 4B affinity column because this would enhance the specificity. It is also possible to use F(ab')$_2$ obtainable by digestion with pepsin or its reduced product Fab'. Thus, the present invention includes such an embodiment wherein the monoclonal and polyclonal antibodies used in the method of this invention may be their specific binding sites F(ab')$_2$ of Fab' as such. Besides this, galactosidase or the like technically available material may be used for this purpose.

The solid phase to be coated with the monoclonal or polyclonal antibody should normally be inert to all the substances used for the antigen-antibody reaction including a liquid vehicle and is selected from a wide variety of inorganic and organic inert carrier materials such as glass, ceramics and resinous materials in the form of a plate or a sphere. Such a solid phase should be homogeneous in quality and identical in size, or otherwise, the quantity of the monoclonal or polyclonal antibody coated on the individual solid phase fluctuates, thus resulting in an inaccurate result of measurements. Because of ease in processing, organic resinous materials such as polystyrene, polyvinyl resin, polyamide resin in the form of a plate or sphere is preferable, with polystyrene balls and polyvinyl chloride plates being most preferable.

Various kinds of buffer solution can be used for the immunoassay of the present invention to provide a definite pH value desirable in the system. A buffer substance used for this purpose is selected from various known compounds having a buffering action, according to the conditions required in the system. Preferable examples of the buffer substances include phosphates, tris-HCl, acetates and amino acids. These substances are used with an acid or sodium chloride at a concentration desired in the system. The operations for the immunization, chromatography, equilibration, fractionation, fluorimetry and spectrophotometry in the method of this invention can be carried out according to the methods known per se for these purposes.

The method of this invention is carried out especially advantageously by using the monoclonal antibody to hPH as the antibody to be coated onto the solid phase and/or the antibody to be labeled with an enzyme.

Our recent immunological tests have revealed that a significant increase in the hPH level is observed in tissue or blood of patients suffering from liver fibrosis caused by hepatic diseases such as chronic hepatitis, liver cirrhosis and alcoholic hepatic disorders.

As will be shown in Table 5 below, the hPH levels in sera from patients with liver cirrhosis as measured in accordance with the method of this invention are significantly higher than those of sera from healthy subjects. According to the present invention, the measurement of blood hPH levels in a simple manner enables foreknowing hepatic diseases, especially liver fibrosis, without relying on biopsy which is burdensome on patients. We have confirmed that fibrosis of hepatic tissues cannot be determined by the conventional liver function tests relying on measurement of the activity of GOT (glutamateoxaloacetate transaminase), GPT (glutamate-pyruvate transaminase), LDH (lactate dehydrogenase), γ-GTP (γ-glutamyl transpeptidase), etc. Thus, the present invention is very useful in the field of diagnosis of hepatic diseases since detection of diseases of this type at an early stage can be expected by the measurement of blood hPH levels according to the method of this invention and since the diagnosis of fibrosis of hepatic tissues can be made by the method of this invention capable of measuring hPH. In addition, the method itself of this invention is simple as compared with the conventional methods and a result obtained by the method of this invention is exact and trustworthy. Thus, the method of this invention is economically advantageous over the conventional methods.

The present invention will now be illustrated in more detail by way of the following examples, but it is to be construed that the scope of this invention is not limited by these specific examples. Among these examples, Examples 1 and 2 illustrate processes for the preparation of the monoclonal antibody and the polyclonal antibody respectively, used in the method of this invention and Examples 3-5 illustrate the method for determining human prolyl 4-hydroxylase by enzyme immunoassay according to the present invention.

EXAMPLE 1

Preparation of mouse anti-hPH monoclonal antibody (a) Preparation of antigen-hPH (EC 1.14.11.2):

Using human placenta as a material, hPH was purified by affinity chromatography on poly-L-proline coupled Sepharose 4B column according to a method of Tuderman et al. described in Eur. J. Biochem. 52, 9-16 (1975), and was then purified with a Bio-Gel A-1.5m (Bio-Rad) column. The hPH preparation obtained was examined for its purity by electrophoresis with the sodium dodecylsulfatepolyacrylamide gel (SDS-PAGE) according to a method of Baum et al. described in J. Virol. 10, 211-219 (1972) whereupon the purity was about 90%.

(b) Preparation of antibody-producing cells:

Three Balb/C female mice of 8 weeks old were subjected to first immunization with the hPH purified in (a) above in a complete Freund adjuvant. 50 μg of hPH as a 0.5 ml solution was intraperitoneally administered to each mouse. Further, the mice were subjected to booster immunization with hPH in the same amount dissolved in physiological saline on the 30th and 60th days. As a final immunization, the mice were subjected to subsidiary immunization on the 90th day by intravenous administration (50 μg/100 μl physiological saline). After 3 days, the mice were killed to extirpate their spleens and the splenocytes were harvested.

(c) Cell fusion:

The following materials and methods were employed:

RPMI 1640 culture medium was prepared by adding sodium bicarbonate (12 mM), sodium pyruvate (1 mM), L-glutamine (2 mM), penicillin G potassium (50 u/ml), streptomycin sulfate (50 μg/ml) and amikacin sulfate (100 μg/ml) to RPMI No. 1640 (Difco Laboratories), adjusting pH to 7.2 with dry ice and sterilizing the mixture by filtration with a 0.2 μm Toyo membrane filter.

NS-1 culture medium was prepared by adding a fetal bovine serum (Granite Diagnostic, Inc.) which had been sterilized by filtration to the RPMI-1640 culture medium above at a concentration of 15% (v/v).

HAT selection medium was the NS-1 culture medium further containing hypoxanthine (100 μM), aminopterine (0.4 μM) and thymidine (16 μM).

HT culture medium was of the same composition as the HAT selection medium except that the aminopterine had been omitted therefrom. PEG 4000 solution was prepared by dissolving polyethylene glycol 4000 (PEG 4000, Merck & Co., Inc.) in the RPMI 1640 culture medium so that a 50% (w/w) non-serum solution was obtained.

The fusion with 8-azaguanine-resistant myeloma cell lines, NS-1 (P3-NS 1-1) was carried out by somewhat modifying the method of Oi et al. described in Selected Method in Cellular Immunology (ed. B. B. Mishell and S. M. Shiigi), W. H. Freeman and Company (1980), 351-372. $1.5 \times 10^8$ karyo-splenocytes (cell viability: 95%) were fused with $2.8 \times 10^7$ cells of NS-1 myeloma cells (cell viability: 95%). The karyo-spleenocytes and myeloma cells were separately washed with the RPMI-1640 culture medium described above. They were suspended in the same culture medium whereby they were mixed in the ratio hereinbefore described for fusion. Using a 50 ml conical test tube made of styrene resin (Corning Glass Works), the mixture in 40 ml of the RPMI-1640 culture medium was centrifuged for 10 minutes at 400 xg to remove the supernatant completely by suction. To the precipitated cells was added dropwise over one minute under gentle agitation 1 ml of the PEG 4000 solution warmed at 37° C. Further gentle agitation was carried out for one minute to resuspend the cells for dispersion. Next, 1 ml of the RPMI-1640 culture medium warmed at 37° C. was added dropwise over one minute. After repeating this operation once, 7 ml of the same culture medium was added dropwise over 2-3 minutes under continuous agitation to effect dispersion of the cells. This mixture was subjected to centrifugal separation for 10 minutes at 400 xg and the supernatant was completely removed by suction. To the precipitated cells was added immediately 10 ml of the NS-1 culture medium warmed at 37° C., and large lumps of cells were carefully pipetted with a 10 ml pipette for dispersion. Further, 20 ml of the same culture medium was added to dilute the dispersion, and it was distributed in a 96-well microplate (Corning Glass Works) made of polystyrene so that $5.9 \times 10^5$ cells/0.1 ml of the culture medium may exist in each well. As a preliminary treatment of the 96-well microplate to be used, 0.2 ml of the NS-1 culture medium was added thereto, and the microplate was warmed overnight in a carbon dioxide incubator (37° C.) and sucked to remove the culture medium just before use. The microplates where the cell fusion has been finished were incubated at a temperature of 37° C. and a humidity of 100% in 7% carbon dioxide/93% air.

(d) Selective culture of the hybridoma in the selection medium:

On the first day of incubation, 2 drops (about 0.1 ml) of the HAT selection medium were added with a Pasteur pipette. On the 2nd, 3rd, 5th, 8th and 11th days, a half of the culture medium (0.1 ml) was replaced by a fresh HAT selection medium. On the 14th day, the culture medium was replaced by the HT culture medium and the same operation was repeated every 3-4 days. The growth of a satisfactory hybridoma (the fusion rate: 3%) was observed usually in 2-3 weeks. All of the wells where the hybridoma has grown, were checked for positivity according to a solid phase-antibody binding test (ELISA) described in the following item (e). 20 cells/288 wells were detected positive. Each positive cell (20 cells/288 wells) detected and 1 ml of an HT culture medium containing $10^7$ mouse thymocytes as a feeder were added to a 24-well plate (Corning Glass Works) made of polystyrene whereby the whole contents of the 20 positive hybridomas detected were transferred. They were incubated in the same manner as in (c) above at 37° C. for about one week in the presence of 7% carbon dioxide. During the incubation, 0.5 ml of the supernatant in each well were replaced once or twice by 0.5 ml of a fresh HT culture medium. At the time the hybridoma had well grown, its positivity was reconfirmed by ELISA and each hybridoma was subjected to cloning according to the limiting dilution method described in the item (f) below. The residual solution after use for cloning was transferred to a 25 cm² tissue culture flask (Corning Glass Works) made of polystyrene to prepare a sample for storage under freezing.

(e) Screening of hybridomas capable of secreting the anti-hPH antibody according to the solid phase-antibody binding test (ELISA):

A method somewhat modifying a method of Rennard et al. described in Anal. Biochem. 104, 205-214 (1980) was employed. This method is suitable for the detection of antibodies from hybridoma. A 96-well microtitration plate (Flow Laboratories, Inc.) was coated with 0.5-1.0 μg of hPH and the others were blocked with 1% bovine serum albumin (BSA). To this was added a part of the supernatant of the hybridoma-grown well, and the incubation was carried out for about one hour at room temperature. A horseradish peroxidase conjugated goat anti-mouse IgG (TAGO, Inc.) as a secondary antibody was added and further incubation was carried out for about one hour at room temperature. Next, hydrogen peroxide and o-phenylene-diamine as a substrate were added, and the degree of the resultant brown color was evaluated qualitatively with naked eyes or the absorbance at 500 nm was determined with a CORONA double wave micro-plate spectrophotometer (MTP-22, Corona Denki Kabushiki Kaisha).

(f) Cloning:

Since there was a possibility of at least 2 kinds of hybridoma being grown in each well, cloning was conducted according to the limiting dilution method to obtain a monoclonal antibody-producing hybridoma. A cloning culture medium was prepared which contained $10^7$ mouse thymocytes as feeder per ml of the NS-1 culture medium, and was added to 36, 36 and 24 wells of a 96-well microtitration plate at 5, 1 and 0.5 hybridomas per each well, respectively. On the 5th and 12th days, about 0.1 ml of NS-1 culture medium was additionally added. A satisfactory growth of the hybridoma was observed 14-15 days after the cloning, and ELISA was carried out for the group where negative colony-forming wells were more than 50%. In case all hybridomas in the tested wells were not positive, the number of colonies in the antibody-positive wells was checked and hybridomas from 4-6 wells were selected from the wells wherein one colony existed and again subjected to cloning. Ultimately, 8 clones were obtained.

(g) Culture in vitro and in vivo of the monoclonal antibody:

The resultant clone was incubated in the NS-1 culture medium or the like proper culture medium (in vitro culture), and a monoclonal antibody could be obtained from the supernatant of the cultivated medium (the concentration of the monoclonal antibody protein: 10-100 μg/ml). In order to obtain the antibody in a larger amount, on the other hand, Pristane, a tumor formation-accelerator (2,6,10,14-tetramethylpentadecane, Aldrich Chemical Company, Inc.), was intraperitoneally administered to the same type animal (Balb/C mouse) as that providing the thymocytes and the myeloma cells in a dose of 0.5 ml per mouse.. After 1-3 weeks, $1 \times 10^7$ cells of hybridoma are also intraperitoneally administered whereby an ascites having a concentration of 4-7 mg protein/ml of the monoclonal antibody can be obtained in vivo after 1-2 weeks.

(h) The isotype of heavy chain and of light chain of the monoclonal antibody:

Each of the resultant ascites was first bound to a microtitration plate coated with hPH in accordance with ELISA described above. After washing, an isotype-specific rabbit anti-mouse Ig antibody (Zymed Laboratories) was added. After washing, horseradish peroxidase labeled goat anti-rabbit IgG (H+L) antibody was added and was then detected with 2,2'-azinodi(3-ethylbenzthiazoline sulfate-6) as a substrate and hydrogen peroxide. The results are arranged and shown in Table 1. Among the investigated antibodies, four antibodies had immunoglobulin chains δ1/κ, one antibody δ2b/κ, two antibodies α/κ and one antibody μ/κ.

Furthermore, each of the resultant monoclonal antibodies was checked for cross-reactivity with hPH subunits by the western blotting method described by Towbin et al. in Proc. Natl. Acad. Sci. USA, 76, 4350–4354 (1979). Four out of the 8 resultant monoclonal antibodies reacted with α chain with molecular weight of 64 KD and the remaining 4 antibodies with β chain with molecular weight of 60 KD (see Table 1; for subunits, see Chen-kiang et al., Proc. Natl. Acad. Sci. USA, 74, 4420–4424, 1977).

(i) Purification of monoclonal antibody:

Each ascites obtained in (g) above was fractionated with ammonium sulfate (40% saturation) and subjected to column chromatography with DEAE-Sephacel (Pharmacia Fine Chemicals) equilibrated with 40 mM phosphate buffer solution, pH 8.0, containing 0.06M sodium chloride to obtain the IgG class in an unabsorbed fraction therefrom. This IgG class was further subjected to gel filtration with a Sephacryl S-300 Superfine (Pharmacia Fine Chemicals) column equilibrated with 50 mM phosphate buffer solution, pH 7.4, containing 0.42M sodium chloride to separate and remove the fetal bovine serum in the culture medium and mouse proteins. The IgA and IgM classes were purified under the same conditions as in the case of other IgG classes except that they were eluted from a DEAE-Sephacel column with a gradient from 0.06M to 1.0M sodium chloride.

EXAMPLE 2

Preparation of antiserum and rabbit anti-hPH polyclonal antibody (a) Immunization:

A female rabbit was subjected to first immunization with the pHP which was isolated and purified from human placenta in the same manner as in Example 1(a), in a complete Freund adjuvant A mixture of 200 μg of hPH and 1 ml of the adjuvant was subcutaneously administered to the back in 15 positions, after which 200 μg of hPH in the complete Freund adjuvant was subcutaneously administered to the back of the rabbit every 2 weeks over the period of 4 months to effect booster immunization. After each booster immunization, a blood sample was taken to check its antiserum for anti-hPH activity in accordance with the method described by Hutton et al. in Anal. Biochem. 16, 384–394 (1966). There was exhibited 56% inhibitory of the activity with 4 μl of the antiserum. This antiserum was judged to be specific to the hPH from the fact that it formed only one precipitin line when subjected to Ouchterlony immunodiffusion and immunoelectrophoresis.

(b) Purification of antiserum:

The rabbit antiserum obtained in (a) above was fractionated with sodium sulfate (18% saturation) and then applied to column chromatography with DEAE-cellulose (DE52, Whatman) equilibrated with 17.5 mM phosphate buffer solution, pH 6.3, to obtain an anti-hPH polyclonal antibody in unabsorbed fractions (purified IgG fractions).

EXAMPLE 3

Sandwich enzyme immunoassay for hPH (a) Procedure for the preparation of rabbit anti-hPH IgG-POD conjugate:

Rabbit anti-hPH IgG-POD conjugate was prepared in accordance with the method described by Ishikawa in J. Immunoassay, 4, 209–327, 1983. The rabbit anti-hPH IgG obtained in Example 2(b) above was dialyzed against 0.1M phosphate buffer solution, pH 6.5. To 0.3–0.5 ml of the rabbit anti-hPH IgG dialyzate was added a 100-fold molar quantity of S-acetylmercaptosuccinic anhydride dissolved in dimethylformamide. The mixture was incubated at 30° C. for 30 minutes. 100 μl of 0.1M Tris-HCl buffer, pH 7.0, 10 μl of 0.1M EDTA solution, pH 6.0, and 100 μl of 1M hydroxylamine solution, pH 7.0 were then added. The mixture was allowed to stand at 30° C. for 5 minutes and then subjected to gel filtration with Sephadex G-25 equilibrated with 0.1M phosphate buffer solution, pH 6.0, containing 5 mM EDTA. In this manner there was obtained SH group-labeled rabbit anti-hPH IgG.

Separately from the procedure described above, horseradish peroxidase (POD) was labeled with a maleimide. Thus, 6 mg of POD was dissolved in 0.1M phosphate buffer solution, pH 7.0, and a 25-fold molar quantity of N-(e-maleimidocaproyloxy) succinimide dissolved in dimethylformamide was added to the solution. The mixture was incubated at 30° C. for 30 minutes. It was then subjected to gel filtration with Sephadex G-25 equilibrated with 0.1M phosphate buffer solution, pH 6.0, to collect maleimide-labeled POD fractions.

To one mole of the above prepared SH group-labeled IgG was added about 5 moles of the maleimide-labeled POD prepared above, and the mixture was allowed to stand at 4° C. for 20 hours. The mixture was then subjected to gel filtration on an Ultrogel AcA 44 (LKB) column equilibrated with 0.1M phosphate buffer, pH 6.5, to collect rabbit anti-hPH IgG-POD conjugate fractions. BSA and thimerosal were added as a stabilizer and a preservative at concentration of 0.1% and 0.005%, respectively, and the fractions were stored at 4° C. until use.

Also for the mouse anti-hPH monoclonal antibodies, the same treatment as described above was applied to prepare corresponding monoclonal antibody IgG-POD conjugates.

(b) Procedure for the preparation of rabbit anti-hPH Fab'-POD conjugate:

Rabbit anti-hPH IgG obtained in Example 2(b) above was dialyzed against 0.1M acetate buffer solution, pH 4.5, containing 0.1M sodium chloride. The thus purified anti-hPH IgG was digested at 37° C. for 24 hours with pepsin added at 2% (w/w) to the antibody. The reaction was terminated with 2M Tris-Hcl buffer solution, pH 8.0, and the reaction mixture was subjected to gel filtration on an Ultrogen AcA 44 column equilibrated with 0.1M phosphate buffer, pH 7.0, to collect F(ab')₂ fractions. The F(ab')₂ fractions were then dialyzed against 0.1M phosphate buffer solution, pH 6.0, to prepare a 0.5–5 mg/450 μl solution. To this solution was added 50 μl of 0.1M mercaptoethylamine dissolved in 0.1M phosphate buffer solution, pH 6.0, containing 5 mM EDTA, and the mixture was incubated at 37° C. for 90 minutes. The mixture was then subjected to gel filtration on an Ultrogel AcA 44 column equilibrated with 0.1M phosphate buffer solution, pH 6.0, containing 5 mM EDTA to collect Fab' fractions. Since the thus prepared Fab' is labile, maleimide-labeled POD prepared in the same manner as in (a) above was added thereto within 24 hours in an amount equimolar to that of the Fab'. 0.1M phosphate buffer solution, pH 6.0, containing 5 mM EDTA was further added so that the respective final concentrations of 50-100 $\mu$M were given. The resultant mixture was allowed to stand at 4° C. for 20 hours or at 30° C. for one hour. The free SH groups were then blocked with N-ethylmaleimide in a 10-fold molar quantity relative to the Fab'. The mixture was subjected to gel filtration on an Ultrogel AcA 44 column equilibrated with 0.1M phosphate buffer solution, pH 6.5, to collect rabbit anti-hPH Fab'-POD conjugate fractions.

Also for the mouse anti-hPH monoclonal antibodies, the same procedure as described above was followed to prepare corresponding monoclonal antibody Fab'-POD conjugates.

(c) Procedure for the determination of ratio of specific binding:

Although the POD labeled antibodies prepared in (a) and (b) above can usually be used as such, i.e. without further purification, it is desirable, where the specific binding ratio (usually 7-8%) is less than 1%, to further purify by specific purification which will be referred to below.

100 ng of the rabbit anti-hPH IgG-POD or rabbit anti-hPH Fab'-POD was first dissolved in 100 $\mu$l of 10 mM phosphate buffer solution, pH 7.0, containing 0.1M sodium chloride and 0.1% BSA and the solution was loaded onto a hPH-coupled Sepharose 4B affinity column (100 $\mu$l gel). The column was washed with 3 ml to 10 mM phosphate buffer solution, pH 7.0, containing 0.1M sodium chloride and 0.1% BSA. The same operation was applied to a BSA-coupled Sepharose 4B column. To a 10 $\mu$l portion of each effluent were added 250 $\mu$l of 0.5% p-hydroxyphenyl-acetic acid (PHPA) dissolved in 50 mM acetate buffer solution, pH 5.0, and 50 $\mu$l of 0.01% aqueous hydrogen peroxide solution, and the mixture was incubated at 30° C. for 10 minutes. 2.5 ml of 0.1M glycine-sodium hydroxide buffer solution, pH 10.3, was added to stop the reaction and the relative fluorescence intensity of the reaction mixture was measured using quinine (1 $\mu$g/ml of 0.1N sulfuric acid) as a control. The difference of the total POD activity of the effluent from the BSA- or hPH-coupled Sepharose 4B column was used to determine the specific binding ratio.

(d) Procedure for affinity purification:

Anti-hPH IgG-POD or anti-hPH Fab'-POD was applied to a hPH-coupled Sepharose 4B column (200 $\mu$l gel) equilibrated with 10 mM phosphate buffer solution, pH 7.0, containing 0.1M sodium chloride and 0.1% BSA, and then the column was washed with 5 ml of the same buffer as described above. Specific antibody was eluted with 500 $\mu$l of 0.1M glycine-HCl buffer solution, pH 2.5 and the effluent was immediately neutralized with 1.0 ml of 0.5M Tris-HCl buffer solution, pH 8.0. The effluent was concentrated to 0.1-0.3 ml and the concentrate was subjected to gel filtration on an Ultrogel AcA 44 column which was previously equilibrated with 0.1M sodium phosphate buffer solution, pH 6.5, containing 0.1% BSA to collect antibody-POD conjugate fractions. After addition of thimerosal, the fractions were stored at 4° C. until use.

With the monoclonal antibodies, which were high in the specific binding ratio, there was no need to apply this affinity purification.

(e) Procedure for the preparation of antibody-coated polystyrene ball:

The mouse anti-hPH monoclonal antibodies and the rabbit anti-hPH polyclonal antibody obtained in Examples 1(i) and 2(b), respectively were individually dissolved in 0.1M phosphate buffer solution, pH 7.5, containing 0.1% sodium azide at a concentration of 0.1 mg/ml. Polystyrene balls (Precision Plastic Ball) were immersed at 4° C. for 24 hours in each of these antibody solutions to coat the polystyrene balls with the respective antibodies. After withdrawing of the free antibody immersion solution, the polystyrene balls were washed, before use, 5 times with "buffer A" (10 mM phosphate buffer, pH 7.0, containing 0.1% BSA, 0.1M sodium chloride and 0.1% sodium azide). Where allowed to stand at 4° C. for one week or more, they were washed again, upon use, three times with buffer A.

(f) Assay procedure:

The polystyrene balls prepared in (e) above were subjected to assay by a fluorimetry method (using balls of 3.2 mm in diameter) and by a colorimetry (using balls of 6.5 mm in diameter).

1) Fluorimetry:

Ten test tubes (8 $\mu$m in inner diameter and 75 mm in length) in duplicate were prepared. 150 $\mu$l portions of the standard hPH preparation purified in Example 1(a) and diluted to concentrations of 0, 0.01, 0.03, 0.1, 0.3, 1, 3, 10, 30 and 100 ng/150 $\mu$l were added individually to the tubes. Ten $\mu$l of human serum and also 140 $\mu$l of buffer A were added to a test tube for sample and mixed well with one another. One antibody-coated ball prepared in Example 3(e) was lightly picked up with a pincette, freed of the adhering liquid by absorbing it with filter paper and put in each test tube. Each test tube was incubated at 37° C. for 1-4 hours with continuous shaking (first reaction; the test tube may, after this reaction, be allowed to stand at 4° C. one day). The reaction solution in each test tube was sucked off, 2-3 ml of a washing solution (10 mM phosphate buffer, pH 7.0 containing 0.1M sodium chloride) was added twice to wash the contents and the washes were removed by suction. Using other test tubes, the enzyme-labeled antibodies prepared in Examples 3(a) and (b), respectively, were diluted with 10 mM phosphate buffer solution, pH 7.0, containing 0.1% BSA and 0.1M sodium chloride to a concentration of 100 ng/150 $\mu$l. The washed polystyrene balls described above were transferred to these test tubes (one ball/tube). It is to be noted that, in the case of the specifically purified enzyme-labeled antibody in Example 3(d) above, a dilution of 10 ng/150 $\mu$l was used. Each test tube was incubated at 20° C. for 3-4 hours with continuous shaking (second reaction) and the unreacted enzyme-labeled antibody solution in each test tube was sucked off and the residue was washed twice with 2-3 ml of a washing solution. To other test tubes was added 100 $\mu$l of 0.1M phosphate buffer solution, pH 7.0 having dissolved therein 0.6% 3-(p-hydroxyphenyl)propionic acid (HPPA) as a POD substrate. The washed polystyrene balls were transferred to these test tubes, one ball for each test tube. Two test tubes containing the POD substrate, HPPA alone were prepared in this reaction step as blank and subsequent operations were also applied thereto. To each of the substrate-placed test tubes was added 50 $\mu$l of 0.015% aqueous hydrogen peroxide solution, and the tubes were incubated at 30° C. for one hour (enzymatic reaction) with continuous shaking. 2.5 ml of 0.1M glycine-sodium hydroxide buffer solution, pH 10.3, was added to stop the reaction. The relative fluorescence intensity was measured with a Hitachi spectrofluorometer (Model 204) using quinine (1 μg/ml of 0.1N sulfuric acid) as a control. Using log-log graph paper with the abscissa indicating the amount in ng of the hPH preparation and the ordinate indicating the relative fluorescence intensity, each measured value for relative fluorescence intensity minus blank value was plotted to draw a standard curve. The amount of hPH per ml of a sample was calculated by multiplying by 100 the reading from the standard curve of the hPH (ng) corresponding to the relative intensity obtained with 10 μl of the sample.

2) Colorimetry:

Ten test tubes (9.5 mm in inner diameter and 105 mm in length) in duplicate were prepared. 300 μl portions of the hPH preparation purified in Example 1(a) and diluted to concentration of 0, 0.01, 0.03, 0.1, 0.3, 1, 3, 10, 30 and 100 ng/300 μl was added individually to the tubes. 10 μl of human serum and also 290 μl of the buffer A were added to a test tube for sample and mixed well with one another. One antibody-coated ball prepared in Example 3(e) was lightly picked up with a pincette, freed of the adhering liquid by absorbing it with filter paper and put in each test tube. Each test tube was incubated at 37° C. for 1-4 hours with continuous shaking (or at 30° C. for 1-2 hours) (first reaction). The reaction solution in each test tube was sucked off, and the residue was washed twice with 2-3 ml portions of the washing solution added. The washed polystyrene balls were transferred to other test tubes each containing 300 μl of a solution containing 10 or 100 ng of one of the enzyme-labeled antibodies prepared in Examples 3(a) and (b) above (one ball/tube). All these test tubes were incubated at 20° C. for 3-4 hours (or at 30° C. for 1-2 hours) with continuous shaking reaction). The unreacted enzyme-labeled antibody solution in each test tube was sucked off and the residue was washed twice with 2-3 ml of the washing solution. To separate test tubes was added 300 μl of 0.1M acetate buffer solution, pH 5.5, having dissolved therein 0.0134% 3,3',5,5'-tetramethylbenzene (TMBZ). The washed polystyrene balls were transferred to these test tubes, (one ball/tube). Two test tubes containing the POD substrate TMBZ alone were prepared in this reaction step as blanks and subsequent operations were also applied thereto. To each of the substrate-placed test tubes was added 100 μl of 0.01% aqueous hydrogen peroxide solution, and the tubes were incubated at 30° C. for 45 minutes with continuous shaking (enzymatic reaction). 600 μl of 1.33N sulfuric acid was then added to stop the reaction. The absorbance at 450 nm was measured with a Shimadzu double beam spectrophotometer (model UV-150-02) using water as a control, and absorbance values for samples minus those for blank were obtained. Calculation of the amount of hPH per ml of the sample was performed in the same manner as in the fluorimetry described in 1) above.

(g) Screening of optimal pair of antibodies for solid phases and conjugates:

Before carrying out assay of hPH by the sandwich method described above, the following screening test was effected to determine optimal combinations of antibodies as solid phase and those as conjugate. The eight monoclonal antibodies and rabbit anti-hPH polyclonal antibody obtained in Examples 1 and 2, respectively, were checked for optimal pair using the standard hPH preparation purified in Example 1(a). The results are shown in Table 2. As for immunoglobulin (Ig)-POD conjugate (enzyme-labeled antibody), pairs of 2-5G8/3-2B12, 2-1C2/3-2B12, 2-6G9/3-2B12 and 2-1C2/rabbit anti-hPH IgG (all expressed as solid phase conjugate) exhibited high ratios (S/N) of specific binding (S) to non-specific binding (N). In the case of Fab'-POD conjugate, high S/N ratios were exhibited with a pair of 3-2B:12/rabbit anti-hPH IgG in addition to the pairs described above. On the basis of these results, standard curves were made with the following solid phase/conjugate: pairs of 2-5G8/monoclonal antibody IgG(3-2B12); 3-2B12/rabbit anti-hPH Fab'; and rabbit anti-hPH IgG / rabbit anti-hPH Fab' (see FIGS. 1 and 2).

FIG. 1 shows an hPH standard curve obtained by the fluorimetry wherein the assay was carried out at 37° C. for one hour for the first reaction; at 20° C. for 3 hours for the second reaction; and at 30° C. for one hour for the third reaction with continuous shaking. In FIG. 1, (—●—) is for the solid phase being rabbit anti-hPH IgG, and (—○—) for the solid phase being monoclonal antibody (3-2B12). In both case, rabbit anti-hPH Fab'-POD was used as the conjugate. (—△—) is for the solid phase being monoclonal antibody (2-5G8) and the conjugate being monoclonal antibody IgG (3-2B12)-POD.

Figure 2:
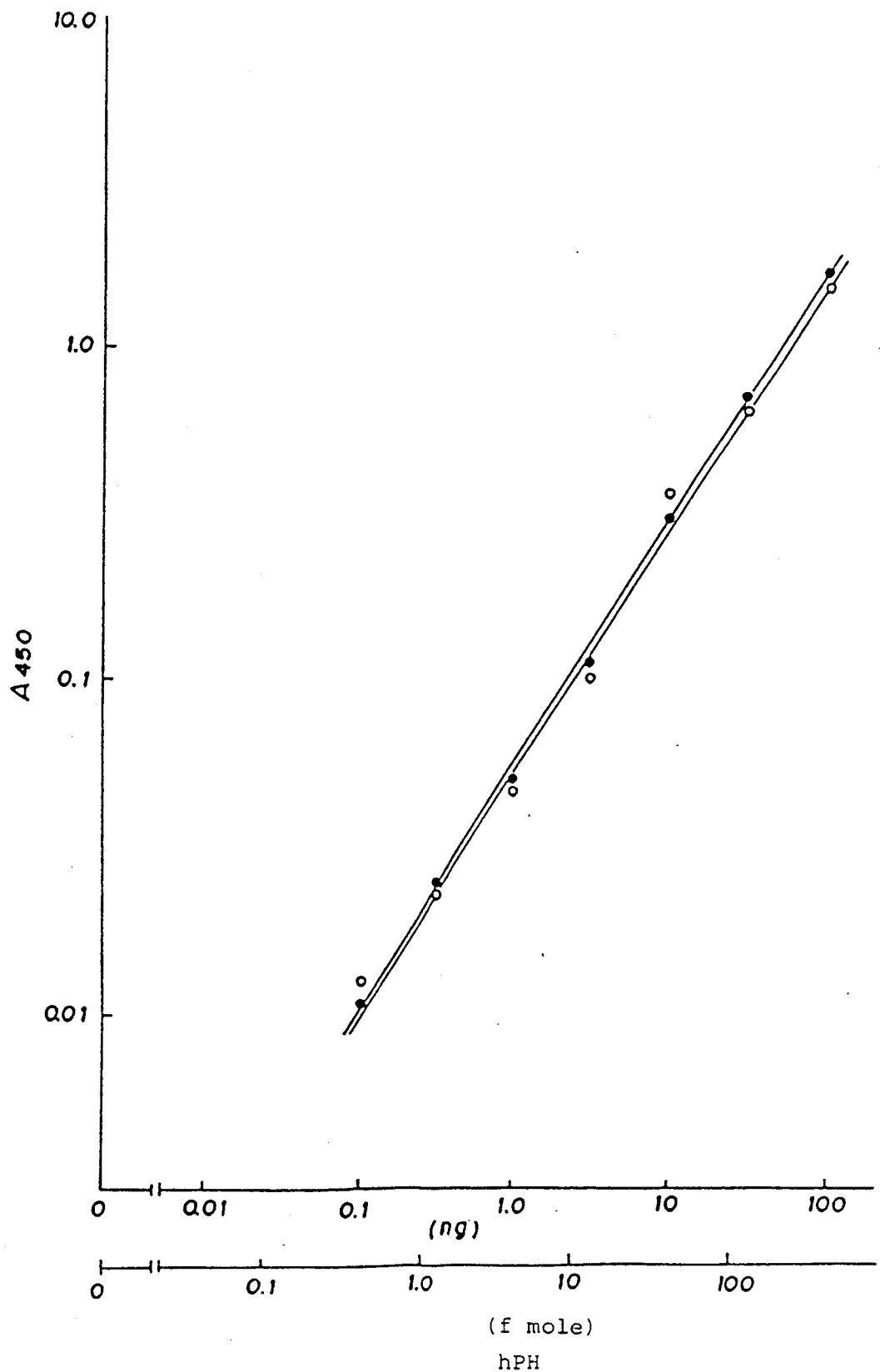

FIG. 2 shows a hPH standard curve obtained by the colorimetry wherein the assay was carried out at 37° C. for one hour for the first reaction; at 20° C. for 3 hours for the second reaction; and at 30° C. for 45 minutes for the third reaction with continuous shaking. In FIG. 2, (—●—) is for the solid phase being rabbit anti-hPH IgG, and (—○—) for the solid phase being monoclonal antibody (3-2B12). In both case rabbit anti-hPH Fab'-POD was used as the conjugate. In both of the fluorimetry and the colorimetry. Linearity was obtained in the range of 0.1-100 ng of hPH per test tube, and the sensitivity was 0.1 ng. Somewhat better sensitivity was observed to be obtained with a pair of both rabbit anti-hPH polyclonal antibodies, for solid phase and conjugate, than with a pair of monoclonal antibody / polyclonal antibody or monoclonal antibody/monoclonal antibody.

Figure 3:
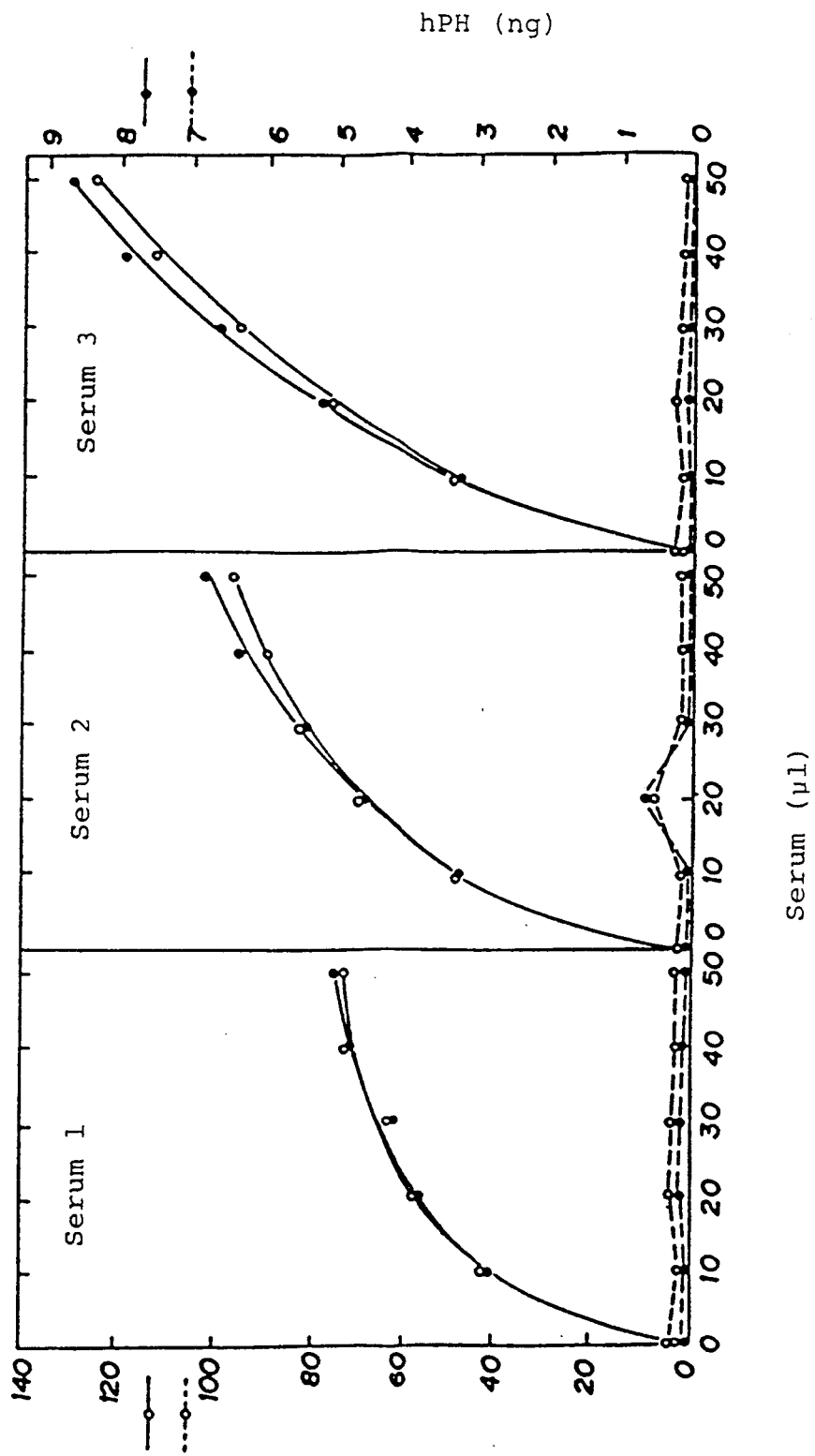
FIG. 3 shows a graph illustrating hPH levels in sera from healthy subjects.

Using 10 μl each of human serum samples from healthy subjects, screening of optimal pair of monoclonal antibodies for solid phase and/or conjugate was carried out (see Table 3). As clearly shown in Table 3, specific binding was extremely low in any of the pairs. On the other hand, where 10 μl each of human serum samples from healthy subjects was likewise used with the both rabbit anti-hPH IgG as solid phase and as conjugate, the fluorescence intensity was found to increase with increasing amounts of the serum. Thus, FIG. 3 depicts hPH levels in 0-50 μl of serum from healthy subject measured by the fluorimetry wherein assay was carried out at 37° C. for one hour for the first reaction; at 20° C. for 4 hours for the second reaction; and at 30° C. for one hour for the third reaction with continuous shaking. In FIG. 3, the solid line (—) is for the solid phase being rabbit anti-hPH IgG and the conjugate being rabbit anti-hPH IgG-POD, and the dotted line (----) is for the solid phase being monoclonal antibody (2-5G8) and the conjugate being monoclonal antibody IgG (3-2B12)-POD. On the other hand, no specific binding was observed when monoclonal antibody (2-5G8) was used as solid phase and monoclonal antibody IgG (3-2B12)-POD as conjugate. Thus these results show that hPH cannot be quantitatively determined with pairs of the monoclonal antibodies alone. Table 4 shows the results obtained when the monoclonal antibodies or rabbit anti-hPH antibody were used individually as solid phase and the rabbit anti-hPH IgG or Fab'-POD as a conjugate. Satisfactory ratios (S/N) of specific binding (S) to non-specific binding (N) resulted when the conjugate was rabbit anti-hPH IgG-POD and the solid phase was clones, 3-2B12, 3-6H5, 2-6G9, 2-7F8 or rabbit anti-hPH IgG. Satisfactory results were also obtained where the conjugate was rabbit anti-hPH Fab'-POD and the solid phase antibody was 3-2B12, 3-4H2 or rabbit anti-hPH IgG. Less non-specific binding was observed with Fab'-POD than with IgG-POD as conjugate.

(h) Determination of hPH levels in sera:

Based on the screening of optimal pair of antibodies for use as solid phase and conjugate antibodies in (g) above, monoclonal antibody IgG(3-2B12) or rabbit anti-hPH antibody IgG was used as solid phase and rabbit anti-hPH Fab'-POD was used as conjugate to determine hPH levels in sera from healthy subjects and patients with liver cirrhosis (see Table 5A). Where the solid phase conjugate combination was a pair of 3-2B12 / rabbit anti-hPH Fab'-POD, the hPH levels in sera from healthy subjects and patients with liver cirrhosis were 95.3 and 151.5 ng/ml, respectively. Thus, significant difference was observed between the two levels (p=0.001). Where the combination was a pair of rabbit anti-hPH IgG / rabbit anti-hPH Fab'-POD the corresponding levels were 92.5 and 142.9 ng/ml, respectively, thus showing significant difference (p=0.05).

EXAMPLE 4

Figure 4:
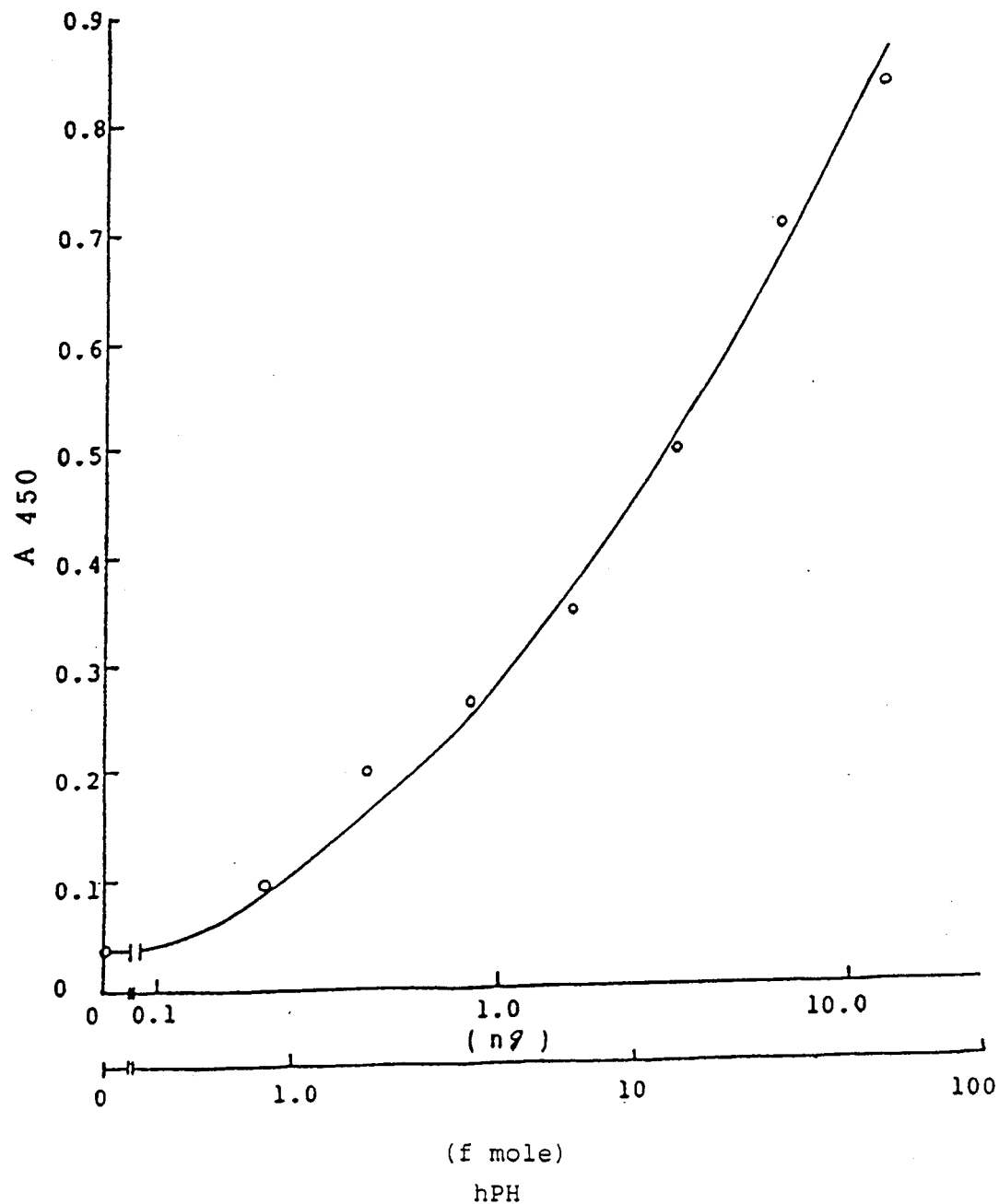
FIG. 4 shows an hPH standard curve on one step assay.

One step assay of hPH using a polyvinyl chloride microtitration plate (Costar) as solid phase 200 μl of 100 g/ml monoclonal antibody (3-2B12) was added to each well of a 96-well polyvinyl plate, and the plate was allowed to stand at 4° C. to coat the wells with the antibody. In carrying out assays, the wells were washed with diluting buffer (10 mM phosphate buffer solution, pH 7.0, containing 0.1% BSA and 0.1M sodium chloride). 20 μl each of a 0, 0.2, 0.4, 0.8, 1.6, 3.2, 6.4 and 12.8 ng/20 μl dilutions of the standard hPH purified in Example 1(a) and 20 μl of serum were individually added to the wells simultaneously with 150 μl of 100 ng/150 μl rabbit anti-hPH Fab'-POD conjugate in the diluting buffer solution described above. The wells were allowed to stand at 37° C. for 2 hours (first reaction). They were then washed three times with 220 μl of 10 mM phosphate buffer solution, pH 7.0, containing 0.1M sodium chloride. 150 μl of 0.0134% TMBZ dissolved in 0.1M acetate buffer solution, pH 5.5, and 50 μl of 0.01% aqueous hydrogen peroxide solution were added, and the plate was incubated at 37° C. for 45 minutes (enzymatic reaction). 180 μl of each reaction solution was transferred into a test tube containing 270 μl of 1.33N sulfuric acid to stop the reaction. After termination of the reaction, the absorbance at 450 nm was measured with a Shimadzu double beam spectrophotometer using water as a control. Using semi-logarithmic graph paper with the abscissa indicating the amount in ng of the hPH and the ordinate indicating the absorbance, all the data were plotted to draw a standard curve. The amount of hPH per ml of a sample was calculated by multiplying by 100 the reading from the standard curve of the hPH corresponding to the absorbance obtained with 20 μl of the sample. In FIG. 4 in the accompanying drawings is shown an hPH standard curve obtained when a monoclonal antibody (3-2B12) was used to coat a 96-well polyvinyl plate and rabbit anti-hPH Fab'-POD was used as conjugate. As is shown in FIG. 4, a curved line is observed in the range of 0–12.8 ng, and the sensitivity was about 0.1 ng. The hPH level in serum was measured for three healthy subjects using this standard curve to give 49.32 and 18 ng/ml serum.

This one step assay technique is suitable for quantitative or qualitative analysis where a great number of samples are needed to be processed, although somewhat inferior in precision to the sandwich two step assay technique using polystyrene balls as a solid support.

EXAMPLE 5

Identification of antigen

Figure 5:
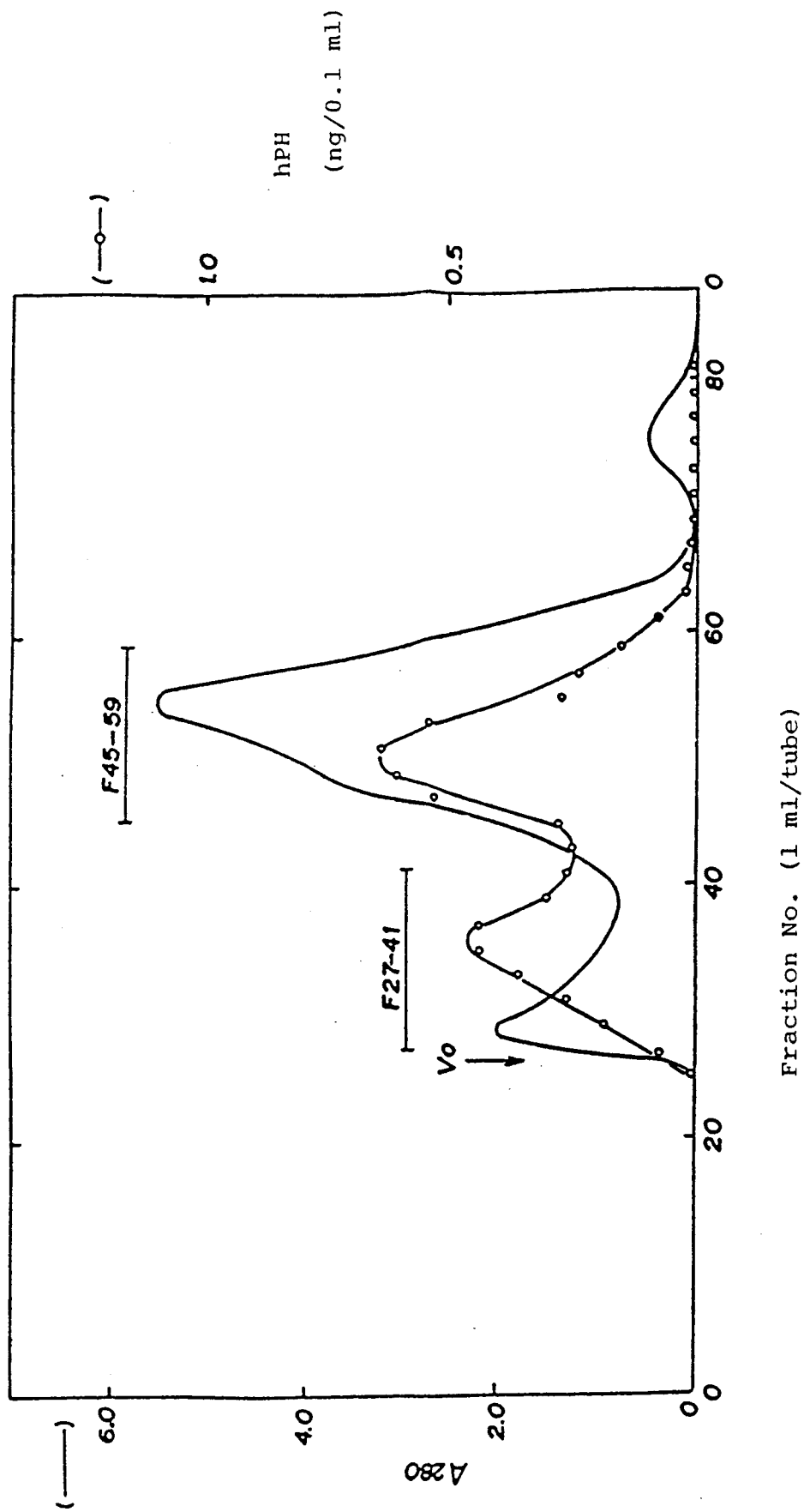
FIG. 5 shows a graph illustrating an elution profile on gel filtration of human sera as well as hPH levels therein.

The following experimentation was conducted to ascertain whether the antigen captured by the sandwich enzyme immunoassay was identical with the hPH isolated in pure form from placenta in Example 1(a). Thus, 1 ml of serum from a patient with hepatic disorder (hPH, 298 ng/ml) was subjected on an Ultrogel AcA 34 gel filtration column (1.5×45 cm) equilibrated with 0.1M phosphate buffer solution, pH 7.0. FIG. 5 in the accompanying drawings shows an elution profile obtained by subjecting human serum on an Ultrogel AcA 34 gel filtration column. In FIG. 5, (—) is for the absorbance at 280 nm and (—o—) is for the hPH level measured with a pair of monoclonal antibody (3-2B12) as a solid phase and rabbit anti-hPH Fab'-POD as a conjugate. As shown in FIG. 5, two peaks of hPH level were eluted at respective (Ve/Vo) values of approximately 1.38 and 1.96. These fractions abundant in hPH were pooled and gel filtration as described above was repeated twice thereto to collect two fractions rich in hPH content (corresponding to 3 ml of serum). The fractions were concentrated by ultrafiltration.

Figure 6:
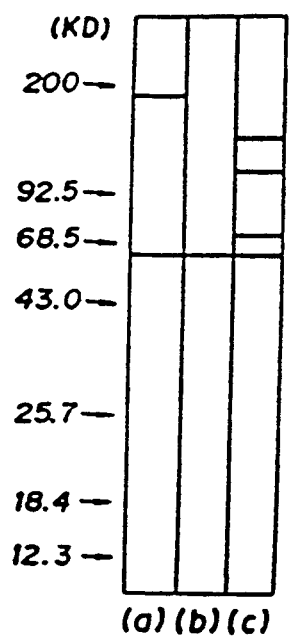
FIG. 6 shows a pattern obtained when hPH fractions were electrophoresed and then transferred to a nitrocellulose sheet.

The concentrated samples described above were subjected to affinity chromatography on a monoclonal antibody (3-2B12)-coupled Sepharose 4B column (0.35×10 cm, 62.4 ng antibody/40 μl gel) to purify hPH in the respective fractions. Thus, the concentrated sample was adsorbed onto the above described affinity column equilibrated with 0.1M phosphate buffer solution, pH 7.0, and the column was washed with 6 ml of the equilibrating buffer solution. The adsorbate in column was then eluted with 300 μl of 0.1M glycine-HCl buffer solution, pH 2.5 into a reservoir containing 300 μl of 2M Tris-HCl buffer solution, pH 8.0. The thus obtained effluents which were derived from the two fractions were dialyzed against 0.1M phosphate buffer solution, pH 7.0, concentrated and then subjected to SDS-PAGE in accordance with the method of Baum et al. described in Example 1(a). After performing SDS-PAGE, proteins was transferred from the acrylamide gel to nitrocellulose sheet (Trans-Blot TM, 0.45 μm, Bio-Rad) by the western blotting method of Towbin et al. described in Example 1(h). This nitrocellulose sheet was treated with a monoclonal antibody IgG (3-2B12)-POD, (specifically reactive with B-subunits, see Table 1), 3,3'-diaminobenzidine and aqueous hydrogen peroxide solution. FIG. 6 in the accompanying drawings shows patterns obtained when two hPH-rich fractions shown in FIG. 5 were each purified on a monoclonal antibody (3-2B12) coupled Sepharose 4B affinity column, subjected to SDS-PAGE and then transferred to nitrocellulose sheet. In FIG. 6, (a) is for purified hPH, (b) for F27-41 fractions in FIG. 5 and (c) for F45-59 fractions in FIG. 5. As reference molecular weights in this experimentation was used a protein marker kit (BRL) containing myosin H chain (200,000), phosphorylase b(92,500), BSA (68,500), ovalbumin (43,000), α-chymotrypsinogen (25,700), β-lactoglobulin (18,400) and cytochrome C (12,300). As shown in FIG. 6, a main band corresponding to β-subunit with molecular weight of 60 KD, and another band corresponding to molecular weight of 170-190 KD were observed with the hPH derived from placenta (see FIG. 6-a). On the other hand, with the 2 fractions corresponding to F27-41 and F45-59 in FIG. 5, there were observed, in addition to a band corresponding to molecular weight of 60 KD, a few bands in the higher molecular region (see FIG. 6-c).

hPH in tissues is said to exist in the form of a tetramer ($\alpha_2\beta_2$) with a molecular weight of 240,000 and consisting of α (64 KD) and β (60 KD) subunits. Although, as clearly shown in FIG. 5, hPH undergoes partial decomposition in blood and therefore its exact subunit composition is not clear, the electroforetic pattern in FIG. 6 suggests that monoclonal antibody (3-2B12) used as solid phase of the immunoassay captured intact or partially decomposed hPH.

TABLE 1

| Clone | Isotype | Chain | Immunocross-reaction with subunit |
|---|---|---|---|
| 2-1C2 | IgG2b | γ2b/κ | α |
| 2-5G8 | IgG1 | γ1/κ | β |
| 2-6G9 | IgA | α/κ | α |
| 2-7F8 | IgA | α/κ | α |
| 3-2B12 | IgG1 | γ1/κ | β |
| 3-3H9 | IgG1 | γ1/κ | β |
| 3-4H2 | IgM | μ/κ | α |
| 3-6H5 | IgG1 | γ1/κ | β |

TABLE 2

| | | Conjugate Nonspecific binding (N) and specific binding (S) with mouse anti-hPH monoclonal antibody (Ig)-POD conjugate | | | | | | | | | | | | | | | | | |
|---|---|---|---|---|---|---|---|---|---|---|---|---|---|---|---|---|---|---|---|
| | | 2-5G8 | | | 3-2B12 | | | 3-3H9 | | | 3-6H5 | | | 2-1C2 | | | 2-7F8 | | |
| Solid Clone | | N Fluorescence intensity | S | S/N | N Fluorescence intensity | S | S/N | N Fluorescence intensity | S | S/N | N Fluorescence intensity | S | S/N | N Fluorescence intensity | S | S/N | N Fluorescence intensity | S | S/N |
| 2-5G8 | IgG1 | 2.1 | 0.5 | 0.2 | 1.4 | 75.6 | 54.0 | — | — | — | — | — | — | — | — | — | — | — | — |
| 3-2B12 | IgG1 | 1.8 | 12.2 | 6.8 | 1.4 | 5.6 | 4.0 | 0.5 | 4.0 | 8.0 | 0.5 | 0 | 0 | — | — | — | 2.8 | 31.2 | 11.1 |
| 3-3H9 | IgG1 | — | — | — | 1.6 | 5.7 | 3.6 | — | — | — | — | — | — | — | — | — | — | — | — |
| 3-6H5 | IgG1 | 1.2 | 1.7 | 1.4 | 1.9 | 9.1 | 4.8 | — | — | — | — | — | — | — | — | — | — | — | — |
| 2-1C2 | IgG2b | 11.0 | 37.0 | 3.4 | 1.4 | 138.6 | 99.0 | 0.9 | 14.1 | 15.7 | 0.9 | 8.7 | 9.7 | — | — | — | — | — | — |
| 2-6G9 | IgA | 11.0 | 29.0 | 2.6 | 1.1 | 52.9 | 48.1 | 0.5 | 10.5 | 21.0 | 0.6 | 2.1 | 3.5 | — | — | — | 2.0 | 0.2 | 0.1 |
| 2-7F8 | IgA | 48.0 | 19.0 | 0.4 | 1.4 | 44.6 | 31.9 | — | — | — | — | — | — | — | — | — | — | — | — |
| 3-4H2 | IgM | 1.3 | 0.3 | 0.2 | — | — | — | — | — | — | — | — | — | — | — | — | — | — | — |
| rabbit anti-hPH | | — | — | — | 10.0 | 27.0 | 2.7 | — | — | — | — | — | — | — | — | — | — | — | — |

| | | Conjugate Nonspecific binding (N) and specific binding (S) with mouse anti-hPH monoclonal antibody (Ig)-POD conjugate | | | | | | Conjugate Nonspecific binding (N) and specific binding (S) for mouse anti-hPH monoclonal antibody (Fab')-POD conjugate | | | | | | | | | | | |
|---|---|---|---|---|---|---|---|---|---|---|---|---|---|---|---|---|---|---|---|
| | | 3-4H2 | | | rabbit anti-hPH | | | 2-5G8 | | | 3-2B12 | | | 3-3H9 | | | 3-6H5 | | |
| Solid Clone | | N Fluorescence intensity | S | S/N | N Fluorescence intensity | S | S/N | N Fluorescence intensity | S | S/N | N Fluorescence intensity | S | S/N | N Fluorescence intensity | S | S/N | N Fluorescence intensity | S | S/N |
| 2-5G8 | IgG1 | — | — | — | — | — | — | — | — | — | 6.0 | 18.0 | 3.0 | — | — | — | — | — | — |
| 3-2B12 | IgG1 | — | — | — | 1.4 | 6.8 | 4.9 | 1.4 | 0.3 | 0.2 | 1.4 | 8.6 | 6.1 | 1.1 | 0.1 | 0.1 | 0.4 | 0.8 | 2.0 |
| 3-3H9 | IgG1 | — | — | — | — | — | — | — | — | — | — | — | — | — | — | — | — | — | — |
| 3-6H5 | IgG1 | — | — | — | — | — | — | — | — | — | — | — | — | — | — | — | — | — | — |
| 2-1C2 | IgG2b | — | — | — | 0.5 | 43.5 | 87.0 | 2.1 | 3.7 | 1.8 | 7.0 | 41.0 | 5.9 | 1.5 | 0.5 | 0.3 | 1.3 | 0.7 | 0.5 |
| 2-6G9 | IgA | — | — | — | 2.3 | 31.7 | 13.8 | 2.4 | 0.4 | 0.2 | 4.1 | 21.9 | 5.3 | 1.7 | 0.2 | 0.1 | 1.5 | 0.1 | 0.1 |
| 2-7F8 | IgA | — | — | — | — | — | — | — | — | — | — | — | — | — | — | — | — | — | — |
| 3-4H2 | IgM | — | — | — | — | — | — | — | — | — | 10.0 | 0.5 | 0.1 | — | — | — | — | — | — |
| rabbit anti-hPH | | — | — | — | — | — | — | — | — | — | — | — | — | — | — | — | — | — | — |

| | | Conjugate Nonspecific binding (N) and specific binding (S) for mouse anti-hPH monoclonal antibody (Fab')-POD conjugate | | | | | | | | | | | |
|---|---|---|---|---|---|---|---|---|---|---|---|---|---|
| | | 2-1C2 | | | 2-7F8 | | | 3-4H2 | | | rabbit anti-hPH | | |
| Solid Clone | | N Fluorescence intensity | S | S/N | N Fluorescence intensity | S | S/N | N Fluorescence intensity | S | S/N | N Fluorescence intensity | S | S/N |
| 2-5G8 | IgG1 | — | — | — | — | — | — | — | — | — | — | — | — |
| 3-2B12 | IgG1 | 5.3 | 11.7 | 2.2 | 0.7 | 0.4 | 0.6 | 0.9 | 0.2 | 0.2 | 0.3 | 1.7 | 5.7 |
| 3-3H9 | IgG1 | — | — | — | — | — | — | — | — | — | — | — | — |
| 3-6H5 | IgG1 | 4.8 | 6.2 | 1.3 | — | — | — | — | — | — | — | — | — |
| 2-1C2 | IgG2b | 7.8 | 2.2 | 0.3 | — | — | — | — | — | — | 0.4 | 2.3 | 5.8 |
| 2-6G9 | IgA | 5.3 | 1.0 | 0.2 | 0.6 | 0 | 0 | 1.5 | 0.1 | 0.1 | 0.8 | 2.7 | 3.4 |
| 2-7F8 | IgA | — | — | — | — | — | — | — | — | — | — | — | — |
| 3-4H2 | IgM | — | — | — | — | — | — | — | — | — | — | — | — |
| rabbit anti-hPH | | — | — | — | — | — | — | — | — | — | — | — | — |

The standard hPH (2.4 ng/tube) was assayed by incubating at 37° C. for 4 hours for the first reaction; at 20° C. for 4 hours for the second reaction; and at 30° C. for one hour for the third reaction using monoclonal or polyclonal antibody-coated polystyrene balls (3.2 mm in diameter).

TABLE 3

Conjugate
Nonspecific binding (N) and specific binding (S) with mouse
anti-hPH monoclonal antibody IgG-POD conjugate

| Solid Clone | | 2-5G8 | | | 3-2B12 | | | 3-3H9 | | | 3-6H5 | | | 2-1C2 | | |
|---|---|---|---|---|---|---|---|---|---|---|---|---|---|---|---|---|
| | | N | S | S/N | N | S | S/N | N | S | S/N | N | S | S/N | N | S | S/N |
| | | Fluorescence intensity | | | Fluorescence intensity | | | Fluorescence intensity | | | Fluorescence intensity | | | Fluorescence intensity | | |
| 2-5G8 | IgG1 | 0.4 | 0 | 0 | 0.5 | 0.4 | 0.8 | 0.8 | 1.5 | 1.9 | 0.9 | 0.8 | 0.9 | 4.1 | 0 | 0 |
| 3-2B12 | IgG1 | 0.7 | 0.1 | 0.1 | 1.1 | 1.4 | 1.3 | 3.0 | 0.4 | 0.4 | 2.2 | 1.7 | 0.8 | 4.9 | 0.5 | 0.1 |
| 3-3H9 | IgG1 | 0.2 | 0.1 | 0.5 | 0.3 | 0.4 | 1.3 | 0.9 | 0.3 | 0.3 | 0.7 | 0.4 | 0.6 | 4.6 | 0 | 0 |
| 2-6G9 | IgA | 7.0 | 1.4 | 0.2 | 0.8 | 1.4 | 1.8 | 1.8 | 1.1 | 0.6 | 1.7 | 1.0 | 0.6 | 3.4 | 0.3 | 0.1 |
| 2-7F8 | IgA | 34.0 | 7.0 | 0.2 | 0.9 | 0.2 | 0.2 | 1.8 | 0.5 | 0.3 | 1.4 | 0.4 | 0.3 | 3.5 | 3.5 | 1.0 |

A 10 μl of serum from a healthy subject was assayed by incubating at 37° C. for one hour for the first reaction; at 20° C. for 3 hours for the second reaction; and at 30° C. for one hour for the third reaction using monoclonal antibodies-coated polystyrene balls (3.2 mm in diameter).

TABLE 4

| Solid Clone | | Conjugate | | | | | |
|---|---|---|---|---|---|---|---|
| | | Rabbit anti-hPH IgG-POD conjugate | | | Rabbit anti-hPH Fab'-POD conjugate | | |
| | | anti-hPH IgG-POD's | | | Anti-hPH Fab'-POD's | | |
| | | nonspecific binding (N) | specific binding (S) | ratio S/N | nonspecific binding (N) | specific binding (S) | ratio S/N |
| | | Fluorescence intensity | | | Fluorescence intensity | | |
| 2-5G8 | IgG1 | 2.4 | 8.6 | 3.6 | 0.1 | 0.3 | 3.0 |
| 3-2B12 | IgG1 | 3.6 | 20.4 | 5.7 | 0.2 | 1.1 | 5.5 |
| 3-3H9 | IgG1 | 2.4 | 9.6 | 4.0 | 0.2 | 0.3 | 1.5 |
| 3-6H5 | IgG1 | 2.4 | 15.6 | 6.5 | 0.2 | 0.4 | 2.0 |
| 2-1C2 | IgG2b | 4.6 | 8.4 | 1.8 | 0.3 | 0.8 | 2.7 |
| 2-6G9 | IgA | 2.3 | 13.7 | 6.0 | 0.4 | 0.7 | 1.8 |
| 2-7F8 | IgA | 1.3 | 17.7 | 13.6 | 0.6 | 0.7 | 1.2 |
| 3-4H2 | IgM | 3.5 | 14.5 | 2.8 | 0.1 | 0.7 | 7.0 |
| rabbit anti-hPH | IgG | 3.7 | 32.3 | 8.7 | 0.2 | 2.9 | 14.5 |

A 10 μl of serum from a healthy subject was assayed by incubating at 37° C. for one hour for the first reaction; at 20° C. for 3 hours for the second reaction; and at 30° C. for one hour for the third reaction using monoclonal or polyclonal antibody coated polystyrene balls (3.2 mm in diameter).

TABLE 5

| | | hPH levels in sera | | | | |
|---|---|---|---|---|---|---|
| Solid | Conjugate | Healthy subjects | n | Patients with liver cirrhosis | n | Difference |
| 3-2B12 | rabbit anti-hPH Fab'-POD | 95.3 ± 52.3 ng/ml | 200 | 151.5 ± 128.5 ng/ml | 25 | significant (P = 0.001) |
| rabbit anti-hPH | rabbit anti-hPH Fab'-POD | 92.5 ± 30.2 | 12 | 142.9 ± 94.1 | 15 | significant (P = 0.05) |

It is understood that the preceding representative examples may be varied within the scope of the present invention, both as to the reagents and immunoassay conditions, by one skilled in the art to achieve essentially the same results.

As many widely different embodiments of this invention may be made without departing from the spirit and scope thereof, it is to be understood that this invention is not limited to the specific embodiments thereof except as defined in the appended claims.

What is claimed is

1. A method for detecting hepatic diseases which are associated with fibrosis by determining the level of human prolyl hydroxylase in a serum sample which comprises:

(a) contacting a serum sample of a patient suspected of having said hepatic disease associated with fibrosis with a monoclonal antibody specific to the β-subunit of human prolyl hydroxylase to form an antigen antibody complex bound on a solid support;

(b) contacting said antigen antibody complex bound on said solid support with an enzyme-labeled monoclonal or enzyme-labeled polyclonal antibody specific to human prolyl hydroxylase to form an antibody antigen enzyme-labeled antibody complex; and (c) measuring the amount of enzyme activity of said bound antibody antigen enzyme-labeled antibody complex to determine the level of human prolyl hydroxylase present in said serum sample and wherein a determination of a level of human prolyl hydroxylase higher than normal is indicative of hepatic disease.

2. The method according to claim 1 wherein said hepatic disease is cirrhosis.

* * * * *